US011026843B2

(12) United States Patent
Werner et al.

(10) Patent No.: US 11,026,843 B2
(45) Date of Patent: Jun. 8, 2021

(54) ACOUSTIC ATTENUATING EAR MUFFS WITH MECHANICALLY ACTUATED ATTENUATION PLUGS

(71) Applicant: INTERNATIONAL BUSINESS MACHINES CORPORATION, Armonk, NY (US)

(72) Inventors: John S. Werner, Fishkill, NY (US); Byron S. Green, Poughkeepsie, NY (US); Arkadiy O. Tsfasman, Wappingers Falls, NY (US); William L. Brodsky, Binghampton, NY (US); Robert K. Mullady, Ulster, NY (US); Jeffrey A. Newcomer, Poughkeepsie, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 453 days.

(21) Appl. No.: 16/010,807

(22) Filed: Jun. 18, 2018

(65) Prior Publication Data
US 2019/0380877 A1    Dec. 19, 2019

(51) Int. Cl.
*A61F 11/14*    (2006.01)

(52) U.S. Cl.
CPC ......... *A61F 11/14* (2013.01); *A61F 2011/145* (2013.01)

(58) Field of Classification Search
CPC .... A61F 11/14; A61F 2011/145; A61F 9/029; H04R 1/1008; H04R 1/1016; H04R 1/1083; H04R 25/65; H04R 25/652; H04R 25/658

USPC ........ 181/129; 381/370, 102, 101, 107, 373, 381/371
See application file for complete search history.

(56) References Cited

U.S. PATENT DOCUMENTS

| 6,970,571 B2 | 11/2005 | Knorr |
| 8,582,796 B2 | 11/2013 | Kimura |
| 8,732,864 B2 | 5/2014 | Fountain |

(Continued)

FOREIGN PATENT DOCUMENTS

WO    9405231 A2    3/1994

OTHER PUBLICATIONS

Berger et al., "Attenuation of Earplugs Worn in Combination with Earmuffs", 1996 (see p. 1). https://pdfs.semanticscholar.org/f23d/605e51f9574057eb478e97cf4e20443ace3e.pdf.

*Primary Examiner* — Melur Ramakrishnaiah
(74) *Attorney, Agent, or Firm* — Cantor Colburn LLP; Teddi Maranzano

(57) ABSTRACT

Acoustic attenuating ear muffs is provided with a first ear pod including a first ear cup having an inner surface and an outer surface, and a first acoustic attenuating member including a first opening coupled to the first ear cup. A second ear pod includes a second ear cup having an inner surface portion and an outer surface portion, and a second acoustic attenuating member including a second opening coupled to the second ear cup. A connecting member links the first ear pod to the second ear pod. A first selectively deployable plug member is arranged between the inner surface and the first acoustic attenuating member. A second selectively deployable plug member is arranged between the inner surface portion and the second acoustic attenuating member.

15 Claims, 5 Drawing Sheets

(56) References Cited

U.S. PATENT DOCUMENTS

| | | |
|---|---|---|
| 8,774,421 B2 | 7/2014 | Kimura |
| 9,636,260 B2 | 5/2017 | Jenkins |
| 2011/0209273 A1* | 9/2011 | Fountain ................. A61F 11/14 |
| | | 2/423 |
| 2014/0211976 A1* | 7/2014 | Brunner ............... H04R 1/1091 |
| | | 381/374 |
| 2017/0252217 A1* | 9/2017 | Gates ...................... A61F 11/08 |
| 2018/0140464 A1* | 5/2018 | Berto ...................... A61F 11/14 |

\* cited by examiner

ACOUSTIC ATTENUATING EAR MUFFS WITH MECHANICALLY ACTUATED ATTENUATION PLUGS

BACKGROUND

Exemplary embodiments relate to the art of wearable acoustic attenuation devices and, more particularly, to a wearable acoustic attenuation device including mechanically actuated plugs.

Ear muffs that attenuate acoustic noise typically include sound insulating pods that fit over a wearer's ears. The sound insulating pods may include one or more layers of insulation that protect a wearer from sounds over a certain decibel level. In other cases, ear protection may take the form of plugs that fit into an entrance of a wearer's ear canal. While effective, conventional ear muffs and ear protection devices may be awkward, uncomfortable, and present a barrier to communication. Particularly in environments in which ear protection is not a continuous need.

SUMMARY

Embodiments of the present invention are directed to acoustic attenuating ear muffs provided with a first ear pod including a first ear cup having an inner surface and an outer surface, and a first acoustic attenuating member including a first opening coupled to the first ear cup. A second ear pod includes a second ear cup having an inner surface portion and an outer surface portion, and a second acoustic attenuating member including a second opening coupled to the second ear cup. A connecting member links the first ear pod to the second ear pod. A first selectively deployable plug member is arranged between the inner surface and the first acoustic attenuating member. A second selectively deployable plug member is arranged between the inner surface portion and the second acoustic attenuating member.

Embodiments of the present invention also include a method of selectively attenuating sound through an ear muff including positioning a first ear pod on a first ear of a wearer and a second ear pod on a second ear of the wearer, urging a first selectively deployable plug member into an first opening formed in a first acoustic attenuating member of the first ear pod, retaining the first selectively deployable plug member in the first opening, urging a second selectively deployable plug member into an second opening formed in a second acoustic attenuating member of the second ear pod, and retaining the second selectively deployable plug member in the second opening.

DETAILED DESCRIPTION

Figure 1:
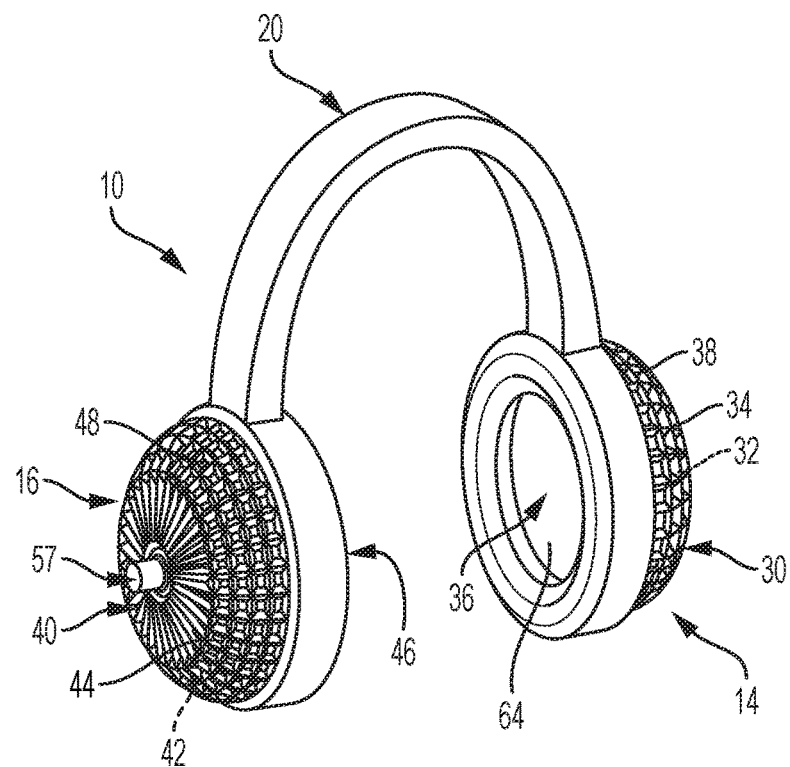
FIG. 1 depicts acoustic attenuating ear muffs having a mechanically actuated attenuation plug, in accordance with an aspect of an exemplary embodiment.

Acoustic attenuating ear muffs, in accordance with an exemplary embodiment, are indicated generally at 10 in FIG. 1. Acoustic attenuating ear muffs 10 include a first ear pod 14 coupled to a second ear pod 16 through a connecting member 20. First ear pod 14 includes a first ear cup 30 having an inner surface 32 and an outer surface 34. A first acoustic attenuating member 36 is disposed at first ear pod 14. A first plurality of openings, one of which is indicated at 38 extend through outer surface 34 and inner surface 32. In this manner, first ear cup 30 includes a mesh surface (not separately labeled) that may provide an amount of ventilation as well as minimal impedance to acoustics.

In a manner similar to that described above with respect to first ear pod 14, second ear pod 16 includes a second ear cup 40 having an inner surface portion 42 and an outer surface portion 44. A second acoustic attenuating member 46 is disposed at second ear pod 16. A second plurality of openings, one of which is indicated at 48, extend through outer surface portion 44 and inner surface portion 42. In this manner, second ear cup 40 includes a mesh surface (not separately labeled) that may provide an amount of ventilation as well as minimal impedance to acoustics. A first selectively mechanically deployable plug assembly 55 (FIG. 2) is provided in first ear pod 14 and a second selectively mechanically deployable plug assembly 57 is arranged in second ear pod 16.

Figure 2:
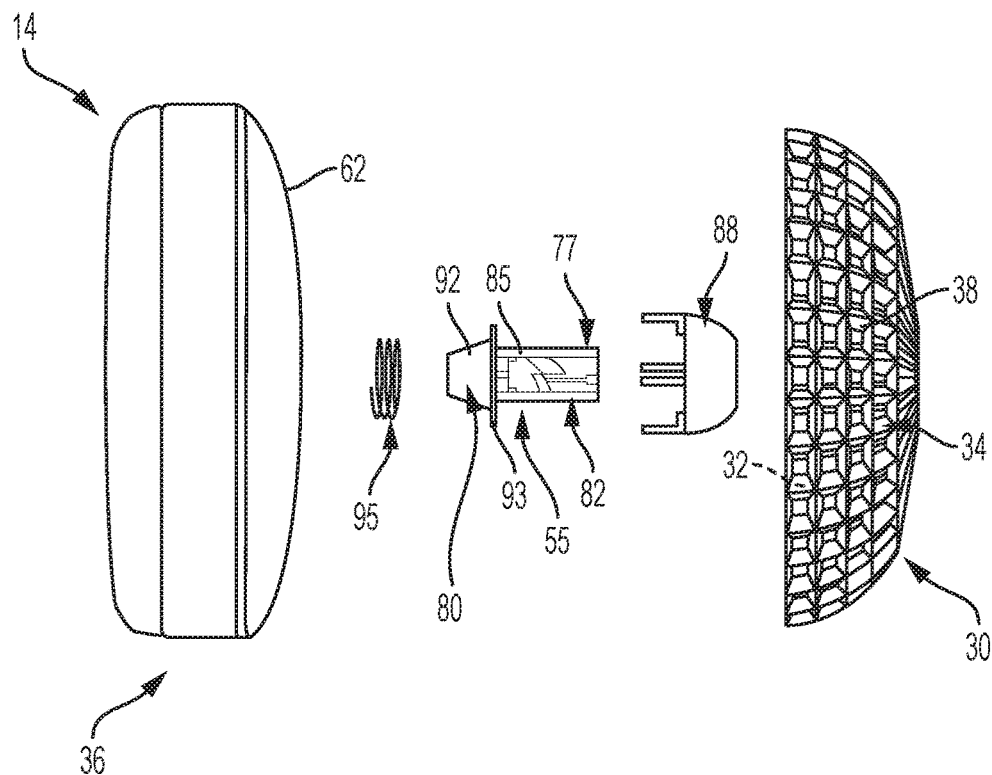
FIG. 2 depicts an unassembled view of the acoustic attenuating ear muffs, in accordance with an aspect of an exemplary embodiment.
Figure 3:
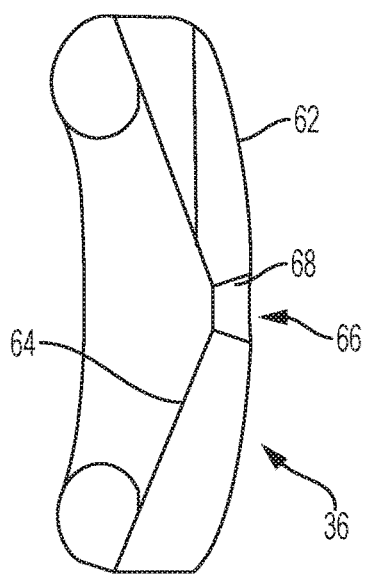
FIG. 3 depicts a cross-sectional side view of an acoustic attenuating member of one of the acoustic ear muffs of FIG. 1.

Reference will now follow to FIGS. 2-3 in describing first ear pod 14 in accordance with an exemplary aspect, with an understanding that second ear pod 16 includes similar structure. First acoustic attenuating member 36 of first ear pod 14 includes an outer surface 62 and an inner surface 64. An opening 66, which may be defined by a tapered wall 68, extends from outer surface 62 through inner surface 64. Opening 66 provides a passage for sounds to pass through first acoustic attenuating member 36. As will be detailed herein, opening 66 is receptive of first selectively deployable plug assembly 55 to prevent the passage of sounds through first acoustic attenuating member 36.

Figure 4:
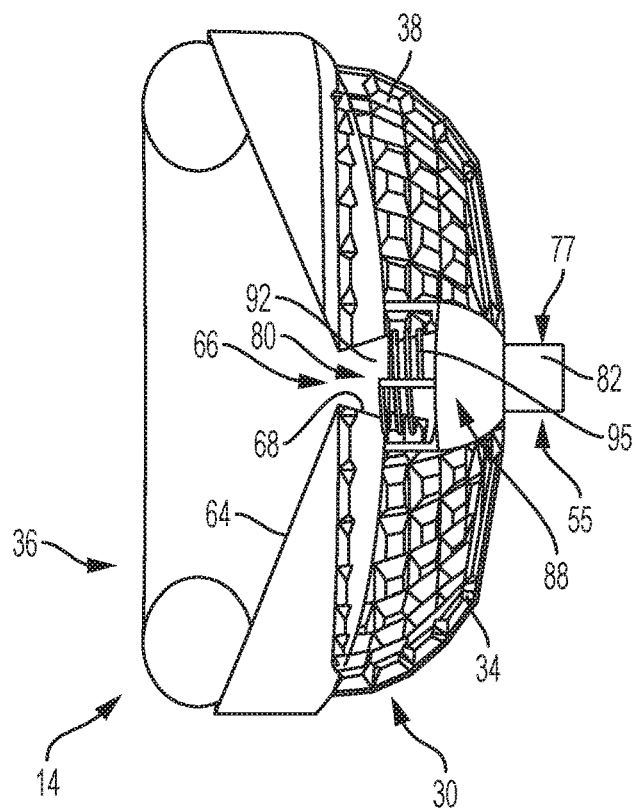
FIG. 4 depicts a partial cross-sectional side view of an acoustic ear muff in an acoustic pass through mode, in accordance with an aspect of an exemplary embodiment.
Figure 5:
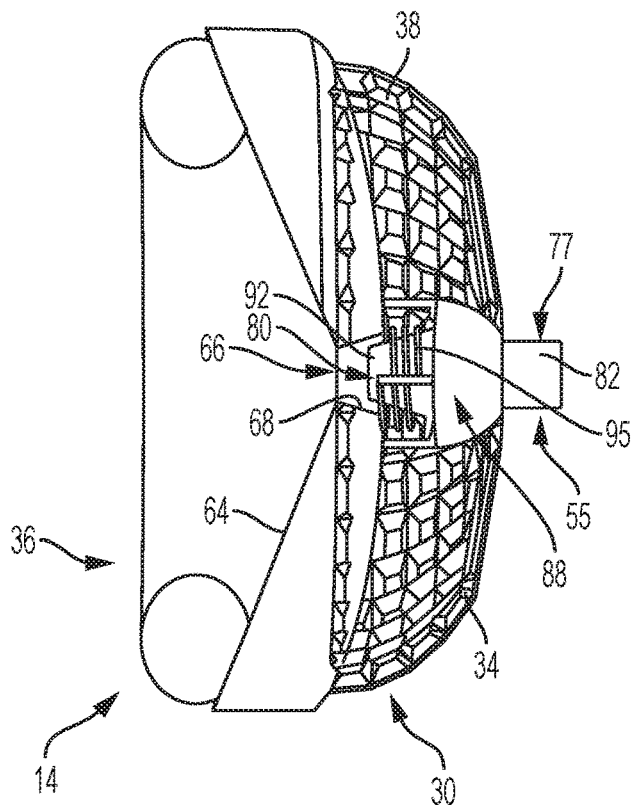
FIG. 5 depicts a partial cross-sectional side view of an acoustic ear muff in a partially acoustic attenuating mode, in accordance with an aspect of an exemplary embodiment.
Figure 6:
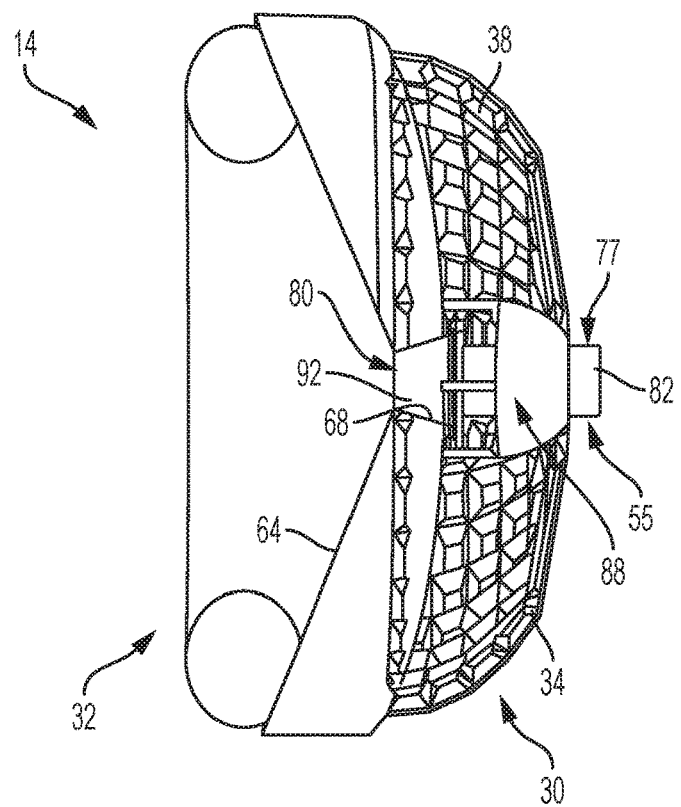
FIG. 6 depicts a partial cross-sectional side view of an acoustic ear muff in fully acoustic attenuated mode, in accordance with an aspect of an exemplary embodiment.

In accordance with an exemplary embodiment, first selectively deployable plug assembly 55 includes a selectively deployable plug member 77 having a plug portion 80 that may be extending into opening 66 and seal against tapered wall 68 and an actuator member 82. Actuator member 82 may be activated by a user to shift plug portion 80 into and out of opening 66. Actuator member 82 may include an actuator profile 85 including two or more actuator positions. Actuator profile 85 enables a user to establish an open or acoustic pass through mode, such as shown in FIG. 4, in which opening 66 is unblocked, a partially attenuating mode, in which opening 66 is partially closed, such as shown in FIG. 5, or closed or an acoustic attenuating position such as shown in FIG. 6 in which opening 66 is sealed. In the partially closed position, plug portion 80 may be positioned in opening 66 to create an acoustic attenuation between the fully open position and the fully closed position. Actuator profile 85 may operate in a manner similar to a push button writing instrument as will be discussed herein In further accordance with an exemplary embodiment, first selectively deployable plug assembly 55 includes an actuator housing 88 that supports selectively deployable plug member 77 at first ear cup 30. Actuator housing 88 includes an opening portion (not separately labeled) that is receptive of actuator member 82. In this manner, actuator member 82 is accessible from outer surface 34.

Plug portion 80 includes a tapered surface 92 that may be guided into opening 66 and provide an amount of sealing. A spring seat 93 is arranged between plug portion 80 and actuator member 82. Spring seat 93 supports a spring 95 that extends about plug portion 80. Spring 95 may be compressed between outer surface section 62 and spring seat 93 to bias selectively deployable plug member 77 between the open or pass through mode, closed or acoustic attenuating mode, and/or partially closed, partial acoustic attenuating mode positions.

Figure 7:
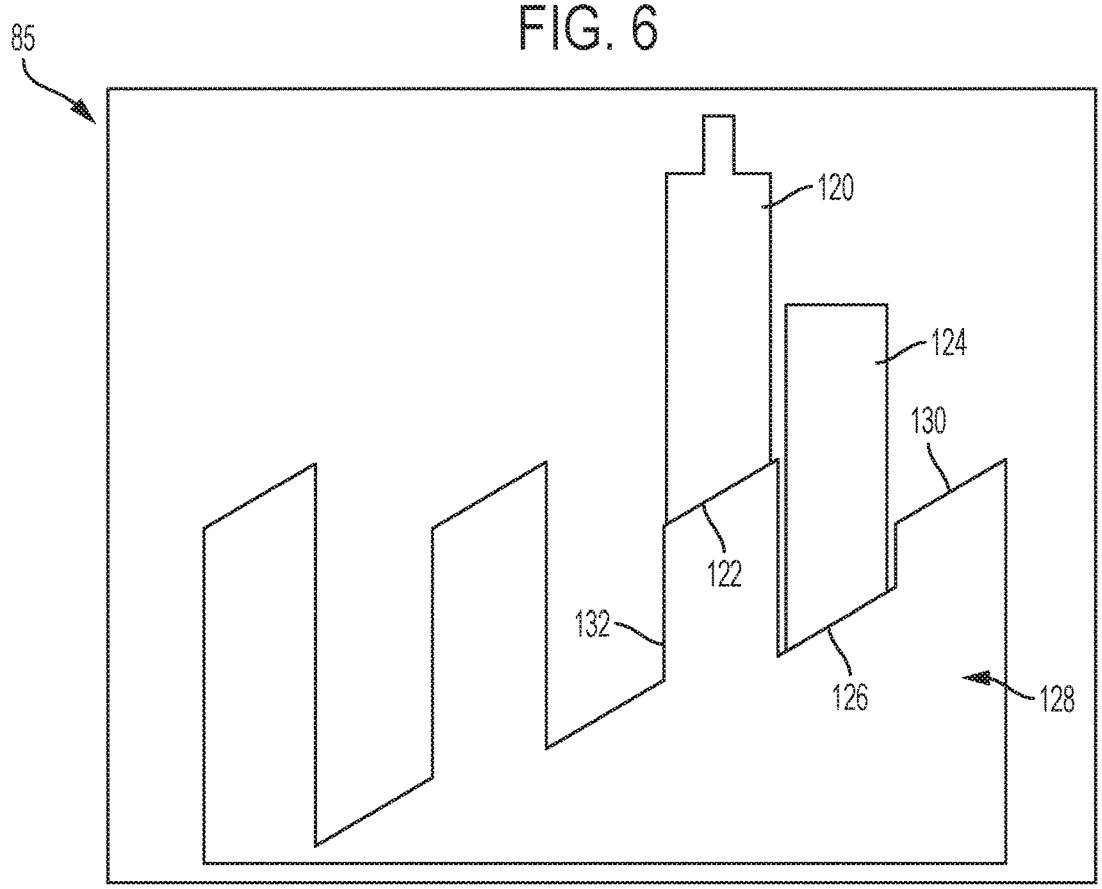
FIG. 7 depicts an actuator member of the acoustic ear muff in the acoustic attenuation mode.
Figure 8:
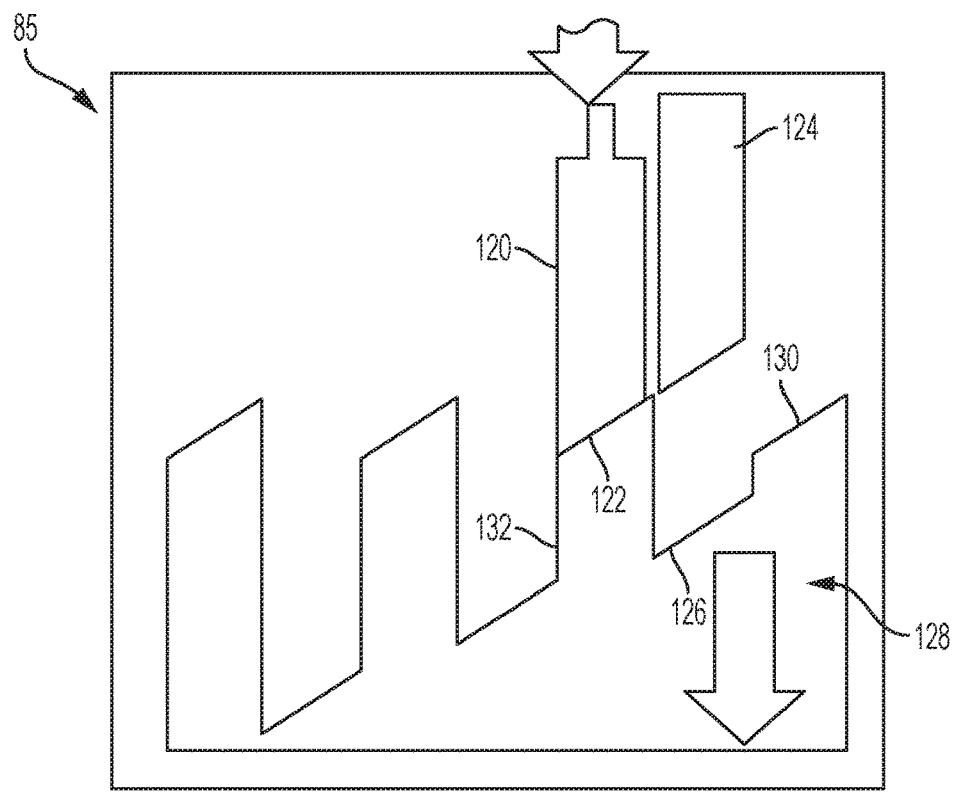
FIG. 8 depicts the actuator member transitioning from the acoustic attenuation mode, in accordance with an exemplary embodiment.

FIGS. 7-10 depict actuator profile in a two dimensional (2-D) representation. As shown in FIG. 7, actuator profile 85 may include a button portion 120 having a first angled surface 122, a fixed portion 124 having a second angled surface 126, and a cam member 128 having a number of angled surface elements, one of which is indicated at 130, and a number of channels, one of which is indicated at 132. Cam member 128 may be slideably mounted on actuator member 82. In FIG. 7, selectively deployable plug assembly 55 is in the acoustic attenuation mode (FIG. 6). If it is desired to change modes, actuator member 82 may be depressed causing first angled surface 122 to push on cam member 128 until first angled surface 122 is below fixed portion 124 such as shown in FIG. 8.

Figure 9:
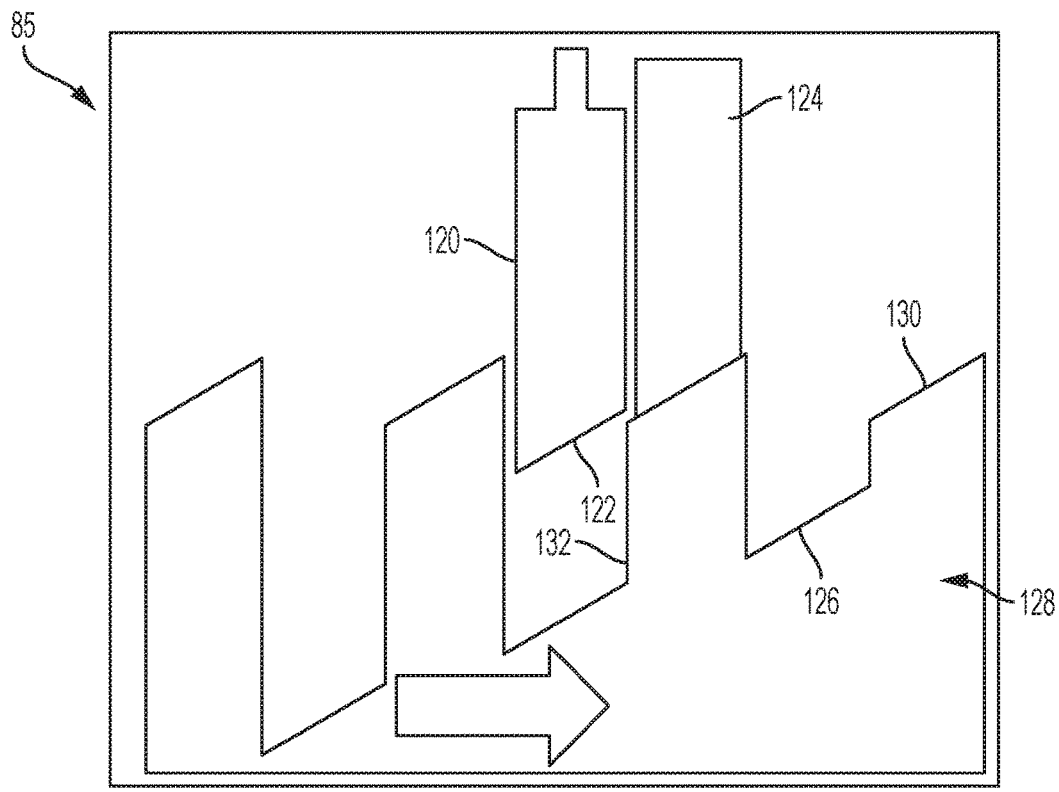
FIG. 9 depicts the actuator member transitioning toward the partial acoustic attenuating mode, in accordance with an exemplary embodiment.
Figure 10:
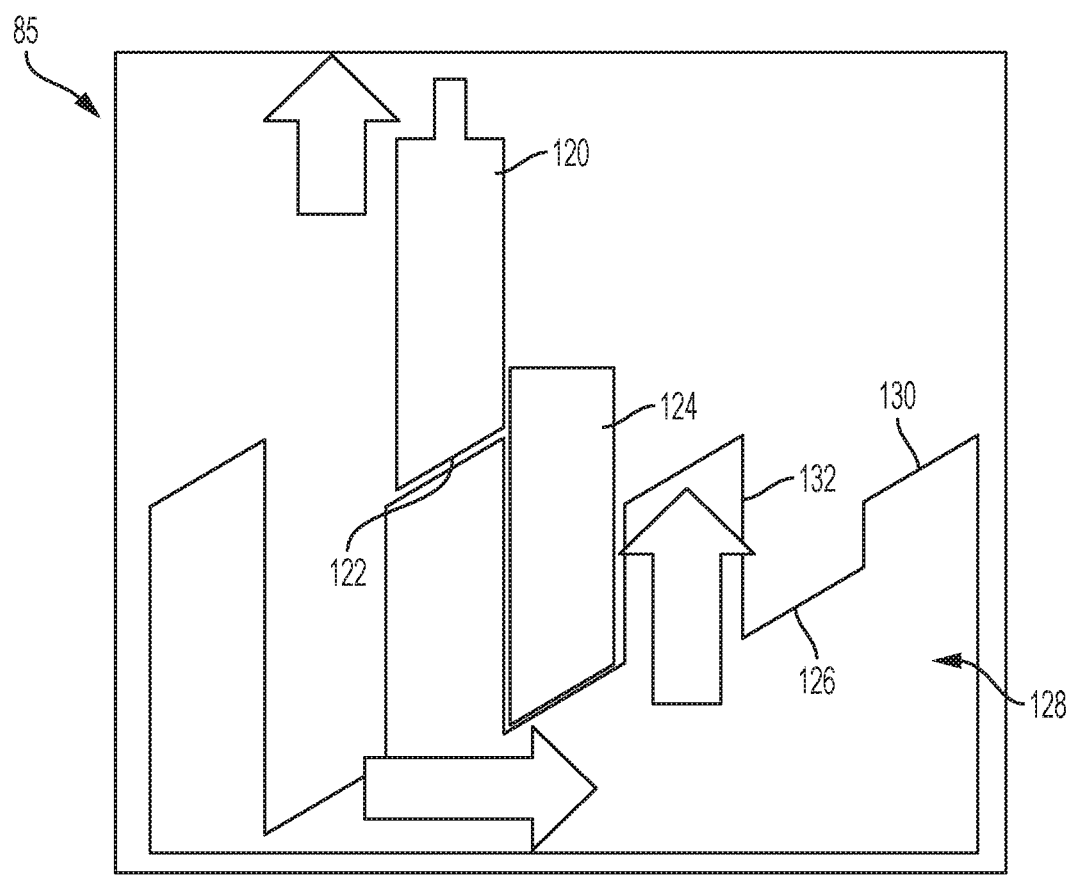
FIG. 10 depicts the actuator member in the partial acoustic attenuating mode, in accordance with an exemplary embodiment.

When first angled surface 122 is below fixed portion 124, cam member 128 rotates causing button portion 120 to enter into one of channels 132 as shown in FIG. 9. At this point, actuator member 82 may be released with spring 95 causing fixed portion 124 to drop into another one of channels 132 and button portion 120 to rest on another cam element 130 as shown in FIG. 10, thereby shifting selectively deployable plug assembly 55 into the partial acoustic attenuating mode such as shown in FIG. 5. A further activation of actuator member 82 would cause selectively deployable plug assembly 55 to shift into an acoustic pass through mode (FIG. 4). Yet another actuation would cause selectively deployable plug assembly to transition back to the acoustic attenuation mode (FIG. 6).

At this point, it should be understood that exemplary embodiments describe an acoustic attenuating ear muff system that allows a wearer to actuate mechanically deployable plugs to selectively shift between a hearing configuration and an acoustic attenuating configuration. Further, the wearer may select to open or close a single ear pod depending upon local conditions. Still further, each ear pod may include an open structure that allows for a clear passage of sound as desired. The open structure also provides for an amount of airflow that may increase an overall comfort level for the wearer.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. Acoustic attenuating ear muffs comprising:
   a first ear pod including a first ear cup having an inner surface and an outer surface and a first acoustic attenuating member including a first opening coupled to the first ear cup;
   a second ear pod including a second ear cup having an inner surface portion and an outer surface portion and a second acoustic attenuating member including a second opening coupled to the second ear cup;
   a connecting member linking the first ear pod to the second ear pod;
   a first selectively deployable plug member arranged between the inner surface and the first acoustic attenuating member; and
   a second selectively deployable plug member arranged between the inner surface portion and the second acoustic attenuating member.

2. The acoustic attenuating ear muffs according to claim 1, further comprising: a first actuator coupled to the first selectively deployable plug member, the first actuator being operable to shift the first selectively deployable plug member between a first position, in which the first opening is unobstructed, and a second position, wherein the first selectively deployable plug member seals the first opening.

3. The acoustic attenuating ear muffs according to claim 2, further comprising: an actuator member accessible from the outer surface and operatively connected to the first actuator for shifting the first selectively deployable plug member between the first position and the second position.

4. The acoustic attenuating ear muffs according to claim 2, wherein the first actuator is operable to shift the first selectively deployable plug member to a third position between the first position and the second position.

5. The acoustic attenuating ear muffs according to claim 2, further comprising: a second actuator coupled to the second selectively deployable plug member, the second actuator being operable to shift the second selectively deployable plug member between a first position, in which the second opening is unobstructed, and a second position, wherein the second selectively deployable plug member seals the first opening.

6. The acoustic attenuating ear muffs according to claim 5, further comprising: an actuator member accessible from the outer surface portion and operatively connected to the first actuator for shifting the second selectively deployable plug member between the first position and the second position.

7. The acoustic attenuating ear muffs according to claim 5, wherein the second actuator is operable to shift the second selectively deployable plug member to a third position between the first position and the second position.

8. The acoustic attenuating ear muffs according to claim 1, wherein the first ear cup includes a first plurality of openings defining a first mesh surface and the second ear cup includes a second plurality of openings defining a second mesh surface.

9. The acoustic attenuating ear muffs according to claim 1, further comprising: a spring mounted to each of the first and second selectively deployable plug members.

10. A method of selectively attenuating sound through an ear muff comprising:
- positioning a first ear pod on a first ear of a wearer and a second ear pod on a second ear of the wearer;
- urging a first selectively deployable plug member into a first opening formed in a first acoustic attenuating member of the first ear pod;
- retaining the first selectively deployable plug member in the first opening;
- urging a second selectively deployable plug member into a second opening formed in a second acoustic attenuating member of the second ear pod; and
- retaining the second selectively deployable plug member in the second opening.

11. The method of claim 10, wherein urging the first selectively deployable plug member includes depressing a first button positioned on an outer surface of the first ear pod.

12. The method of claim 11, further comprising: selectively releasing the first selectively deployable plug member from the first opening.

13. The method of claim 12, wherein selectively releasing the first selectively deployable plug member includes further depressing the first button.

14. The method of claim 10, further comprising: biasing the first selectively deployable plug member away from the first opening.

15. The method of claim 10, further comprising: passing sound through one or more openings formed through an outer surface of the first ear pod and through the first opening into the first ear.

* * * * *